(12) United States Patent  (10) Patent No.: US 8,911,386 B2
Zacharopoulos  (45) Date of Patent: Dec. 16, 2014

(54) RESPIRATORY COMPRESSION BELT

(76) Inventor: Nicholas G. Zacharopoulos, New City, NY (US)

( * ) Notice: Subject to any disclaimer, the term of this patent is extended or adjusted under 35 U.S.C. 154(b) by 240 days.

(21) Appl. No.: 13/150,767

(22) Filed: Jun. 1, 2011

(65) Prior Publication Data

US 2012/0310127 A1 Dec. 6, 2012

(51) Int. Cl.
*A61H 7/00* (2006.01)
(52) U.S. Cl.
USPC .................................. 601/84; 601/13; 601/19
(58) Field of Classification Search
USPC ............ 601/41–44, 148–152, 84; 602/13, 14, 602/19, 53, 55, 67, 62, 47, 58, 59, 61; 2/44; 128/903
See application file for complete search history.

(56) References Cited

U.S. PATENT DOCUMENTS

| 4,135,503 | A | * | 1/1979 | Romano | 602/13 |
| 4,682,587 | A | * | 7/1987 | Curlee | 602/13 |
| 5,349,706 | A | * | 9/1994 | Keer | 2/300 |
| 5,514,155 | A | * | 5/1996 | Daneshvar | 606/201 |

* cited by examiner

*Primary Examiner* — Michael A. Brown
(74) *Attorney, Agent, or Firm* — Donald J. Ranft; Collen IP

(57) ABSTRACT

A device and method for restricting the respiratory movement of a patient undergoing medical treatment. A respiratory compression belt is positioned properly, secured on the patient and pressurized to control patient movement.

6 Claims, 6 Drawing Sheets

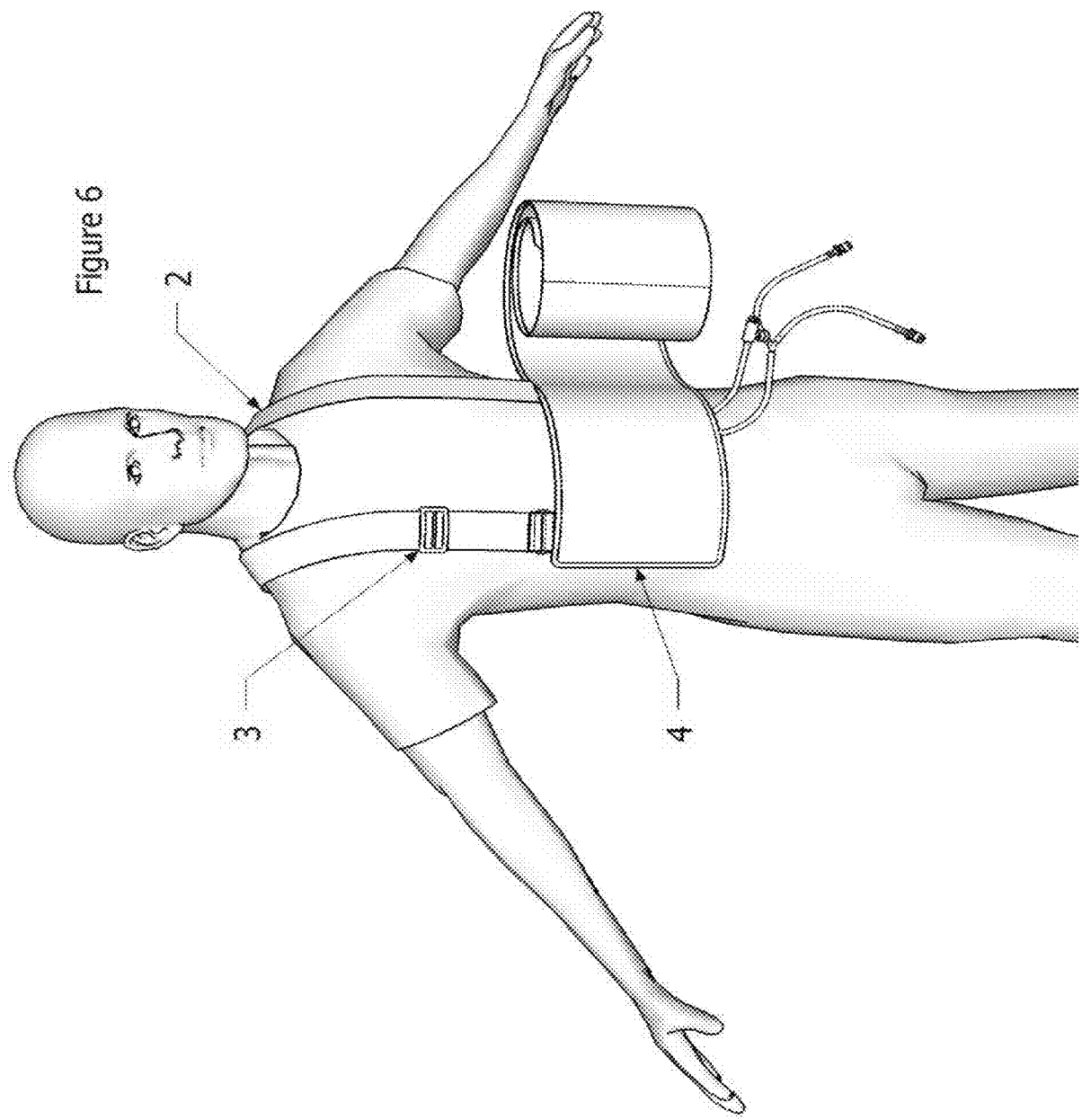

RESPIRATORY COMPRESSION BELT

BACKGROUND

It is critical that any movement of a patient undergoing certain medical procedures be restricted to as little as possible. For example the respiratory motion of patients undergoing hypo-fractionate or single fraction stereotactic radiotherapy for liver or other abdominal cancers.

Existing devices which attempt to minimize movement of the patient due to respiration use an approach involving a small plate typically 5" wide which is pressed up against the patient's abdomen. This plate is in all cases held over the patient with an arch of some sort and the plate can then be pushed up against the patient.

The problem with this approach is that it only applies pressure in one direction, which just allows the internal organs to be displaced laterally instead of held still.

SUMMARY

The respiratory compressor belt reduces respiratory motion of patients undergoing medical treatments such as hypo-fractionated or single fraction stereotactic radiotherapy for liver or other abdominal cancers by applying pressure evenly around the entire periphery of the patient.

DETAILED DESCRIPTION OF DRAWINGS

FIG. 6 depicts a respiratory compression belt being placed on a patient.

DETAILED DESCRIPTION

Figure 1:
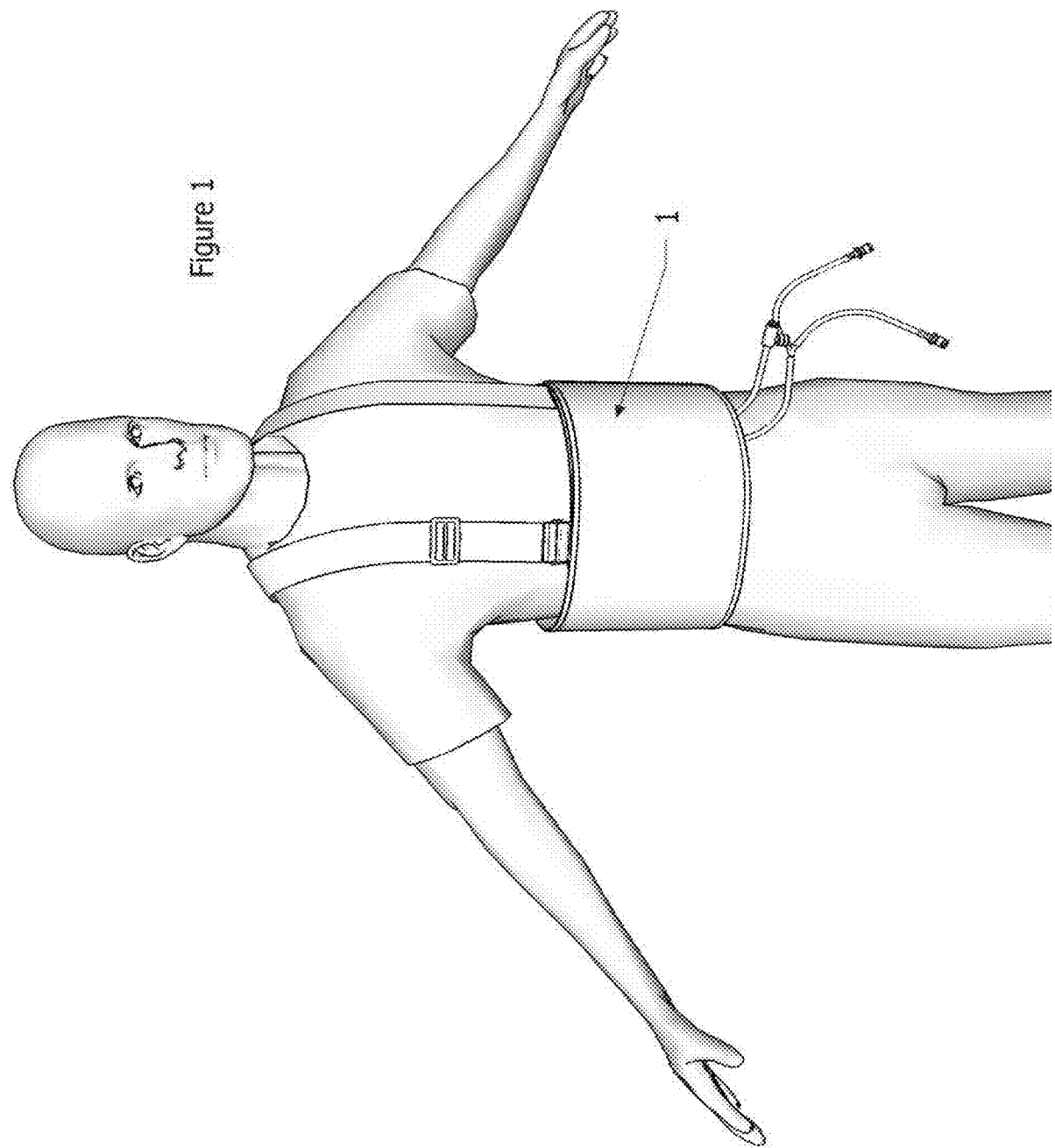
FIG. 1 depicts a respiratory compression belt strapped onto a patient.
Figure 2:
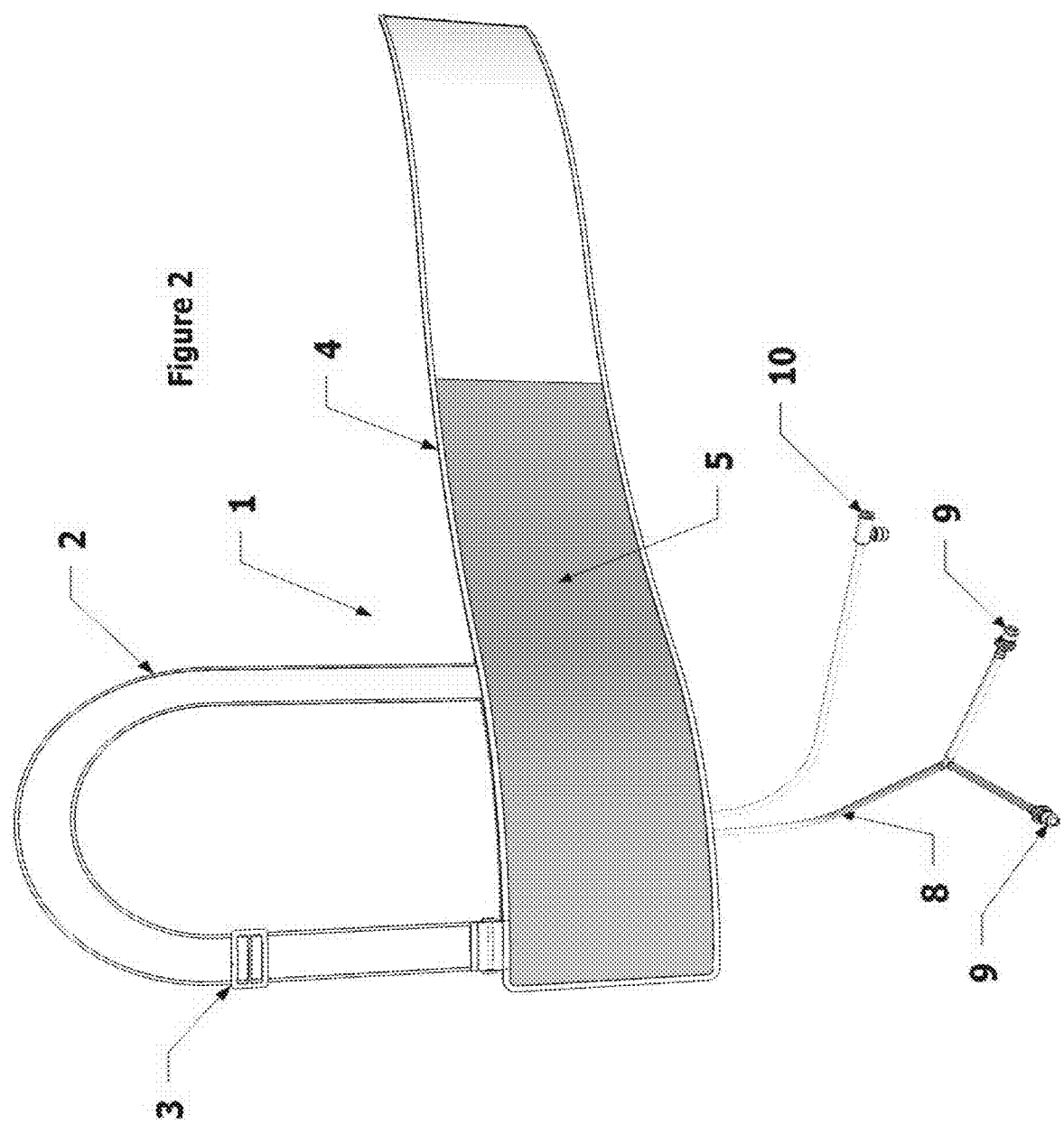
FIG. 2 depicts a front view of an opened respiratory compression belt.
Figure 3:
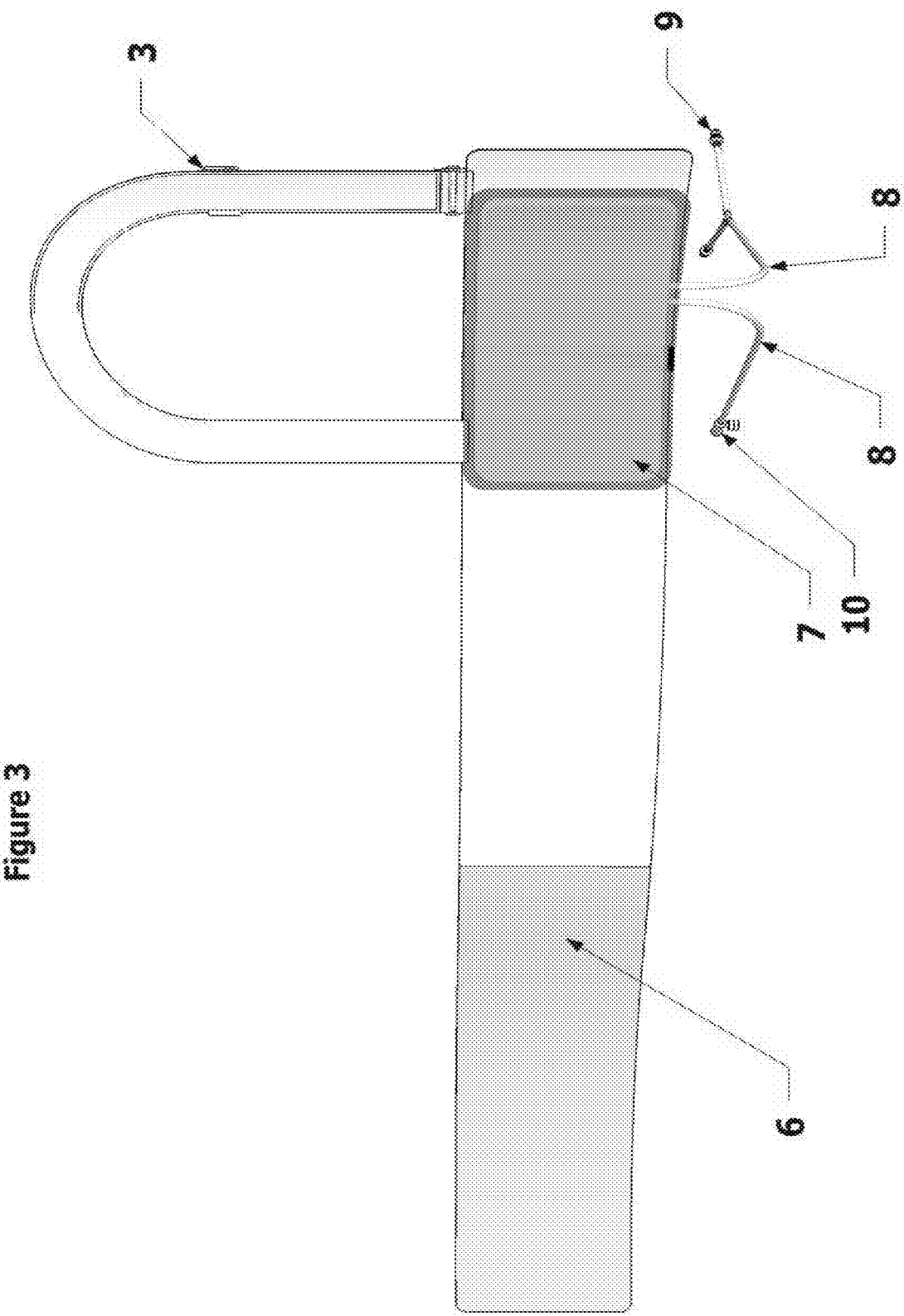
FIG. 3 depicts a rear view of an opened respiratory compression belt.

As shown in FIG. 1 a respiratory compression belt is designed to be wrapped around a patient. FIGS. 1 and 2 identify the major components of a respiratory compression belt (1). A patient strap (2) is placed over the patient's head to rest on patient's shoulders. An adjustment mechanism (3) is provided to allow positioning of the belt (4) in the appropriate position on a patient in relation to the patient's respiratory system. The belt (5) includes a means to secure the belt around the patient. FIGS. 2 and 3 depict the use of a loop surface (5) and a hook surface (6) to secure the belt (4). An expandable pouch with a bladder (7) is provided to enable the use of air or other gas pressure to tighten the belt and minimize respiratory movement of the patient as warrants. One or more tubes (8) are connected directly to the bladder (7). The end of each tube (8) which is connected to the bladder has a quick connection mechanism (9) attached. FIG. 2 includes a tube directly connected to the bladder with a pressure release valve (10) at its end.

Figure 4:
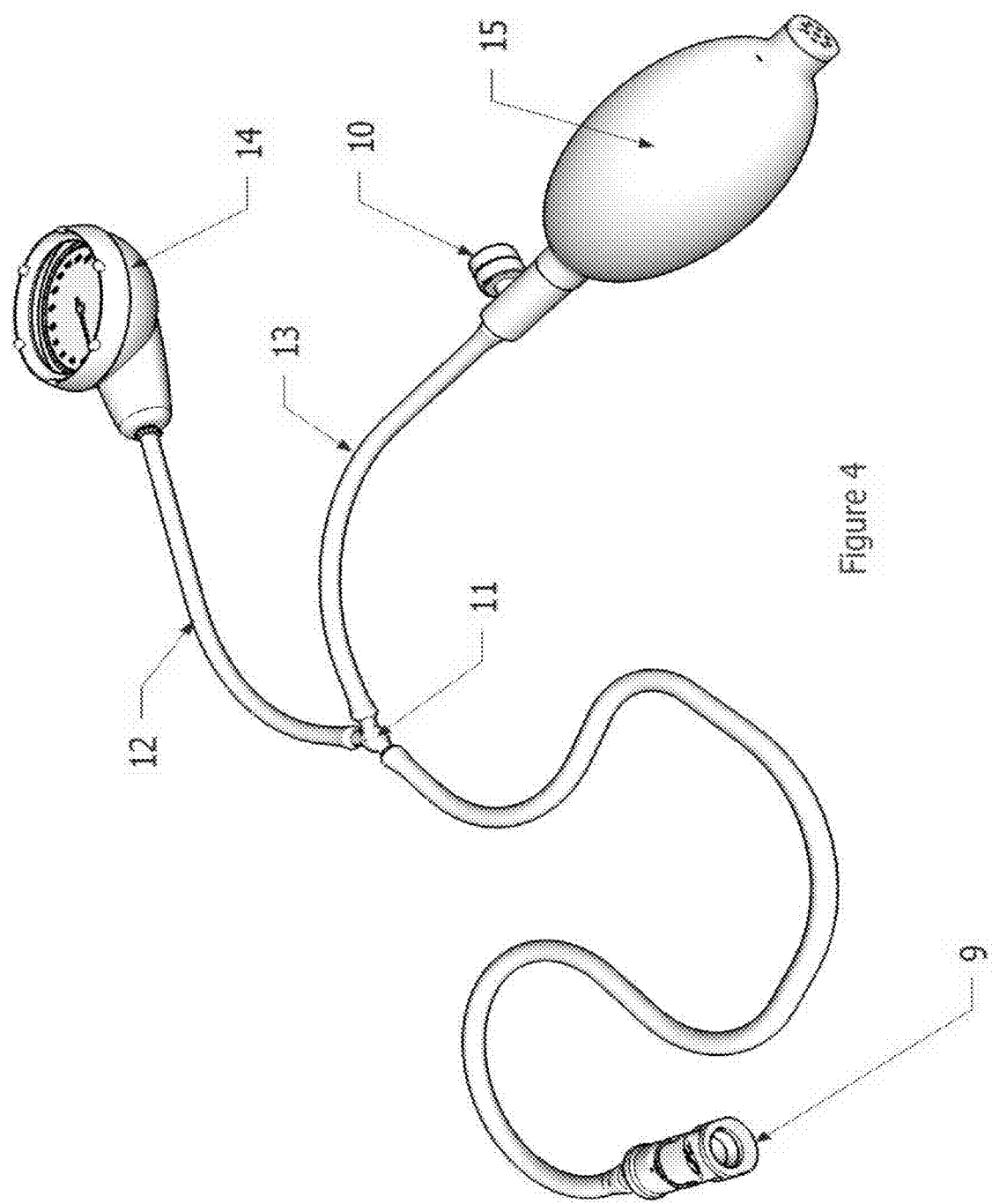
FIG. 4 depicts a bulb-gauge assembly.

FIG. 4 shows a possible configuration for connection to a tube (8) which is directly connected to the bladder (7). The tube (8) can be split into multiple branches as desired. FIG. 4 shows the tube (8) being split by a "Y" fitting into 2 separate branches (12 and 13). A pressure gauge (14) is attached to one branch (12) and a bulb (15) to manually increase pressure in the bladder (7) attached to the other branch (13). As shown in FIG. 4 a pressure release valve can be installed on any tube directly connected to the bladder.

Figure 5:
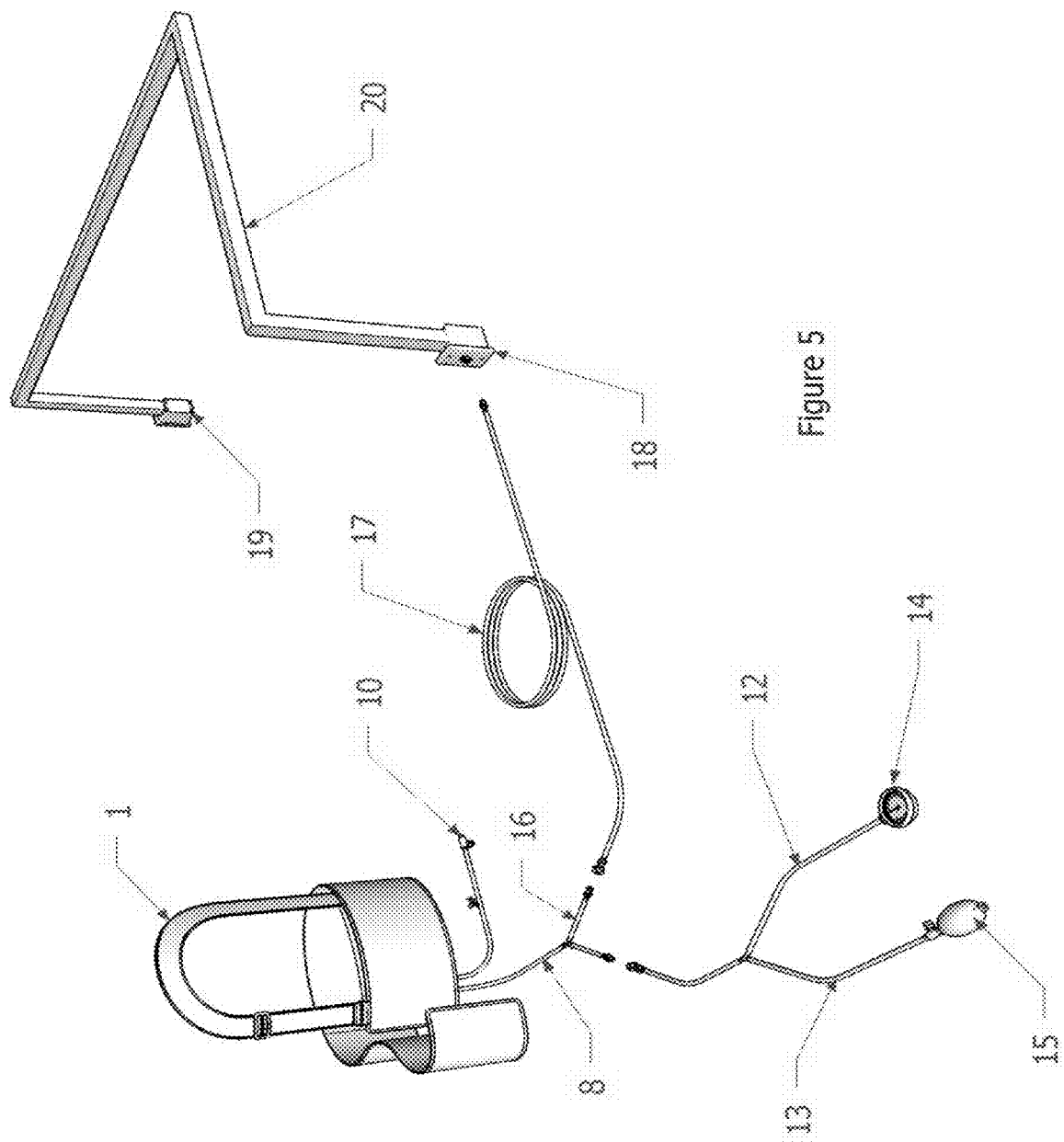
FIG. 5 depicts typical components required to allow remote monitoring and control of bladder pressure.

FIG. 5 further includes an additional branch (16) off the tube (8) which is directly connected to the bladder (7). The branch can be connected to tubing (17) which is run to an appropriate wall mount plate (18) in the treatment room. Additional tubing is run to a wall mount plate (19) in the control room. This tubing can be run in conduit (20) if warranted. Additional means to monitor and control pressure can then be connected to the wall mount plate (18) in the control room.

In lieu of one ore more tubes extending from the bladder, one or more connection device(s) can be provided at the wall of the bladder.

The configuration of the local and remote means for monitoring and controlling pressure can be easily modified to be compatible with the facility in which the respiratory compression belt is to be used. The components used can also be selected as desired for a particular configuration. For example other means for pressurization in lieu of a manual bulb can be used. In lieu of a manual gauge to monitor pressure electronic measurement and display instruments can be used with cabling or wireless transmission means provided as warranted. If desired pressure instrumentation can alert appropriate personnel to changes in pressure.

To use a respiratory compressor belt (1) the strap (2) is placed over the patient's head as shown in FIG. 6. The strap adjustment mechanism (3) is utilized to ensure the belt is positioned properly on the patient. The belt (4) is then wrapped around the patient and secured utilizing a hook and loop means or any other means to ensure the belt is secure on the patient before and during pressurization.

After the patient with respiratory compressor belt is positioned on the treatment table the appropriate components for local and remote (if desired) monitoring and control and connected to the appropriate tube(s) connected to the bladder. Pressure release valve(s) are closed and pressure in the bladder is increased to an appropriate value. Pressure is continuously monitored and increased or decreased as warranted. When treatment is completed the pressure release valve(s) are opened, the connections to the tube(s) directly connected to the bladder are removed and the patient can remove the respiratory compressor belt.

Although several embodiments described above and by the claims serve to illustrate various concepts, components and techniques which are the subject of this patent, it is apparent to those of ordinary skill in the art that other embodiments incorporating these concepts, components and techniques may be used. It is understood that the scope of the following claims are not limited to the described embodiments and that many modifications and embodiments are intended to be included within the scope of the following claims. In addition the specific terms utilized in the disclosure and claims are used in a generic and descriptive sense and not for the purpose of limiting the invention described in the following claims.

The invention claimed is:

1. A respiratory compressor belt comprising
a belt designed to wrap around a patient;
a strap attached to the belt and designed to support the respiratory compressor belt on a patient's shoulders;
an adjustment mechanism for the respiratory compressor belt
a bladder attached to the belt
at least one tube directly connected to the bladder to allow pressurization and depressurization of the bladder;
a connection means attached to each tube; and a means for monitor and control of pressure in the bladder in a separate room from the room where the patient with respiratory compressor belt is located.

2. A respiratory compressor belt according to claim 1 in which electrical cabling is used for the transmission of signals for monitoring and control of bladder pressure.

3. A respiratory compressor belt according to claim 1 in which the electrical signals for monitoring and control of bladder pressure are transmitted using wireless means.

4. A method for restricting the respiratory movement of a patient comprising
   selecting a respiratory compressor belt;
   placing a strap of the respiratory compressor belt over the patient's shoulders;
   adjusting the strap to ensure the respiratory compressor belt is in the proper location on the patient;
   wrapping the belt around the patient and securing it;
   positioning the patient in a desired location for a medical procedure to be performed;
   connecting a means for monitor and control pressure in a bladder attached to the belt of the respiratory compressor belt; and
   connecting a means for monitor and control of pressure in the bladder in a separate room from the room where the patient with respiratory compressor belt is located.

5. A method for restricting respiratory movement according to claim 4 in which electrical cabling is used for the transmission of signals for monitoring and control of bladder pressure.

6. A method for restricting respiratory movement according to claim 4 in which the electrical signals for monitoring and control of bladder pressure are transmitted using wireless means.

\* \* \* \* \*